United States Patent [19]

Ishino et al.

[11] Patent Number: 5,214,041
[45] Date of Patent: May 25, 1993

[54] HAIR REVITALIZING TONIC COMPOSITION

[75] Inventors: Akihiro Ishino; Kiyoshi Miyazawa; Seishiro Fujii, all of Yokohama, Japan

[73] Assignee: Shiseido Company Ltd., Ginza, Japan

[21] Appl. No.: 655,363

[22] PCT Filed: Jun. 12, 1990

[86] PCT No.: PCT/JP90/00765
§ 371 Date: Apr. 8, 1991
§ 102(e) Date: Apr. 8, 1991

[87] PCT Pub. No.: WO90/15588
PCT Pub. Date: Dec. 27, 1990

[30] Foreign Application Priority Data
Jun. 12, 1989 [JP] Japan .................. 1-148617

[51] Int. Cl.$^5$ .............................. A61K 31/54
[52] U.S. Cl. .................. 514/223.5; 514/223.2; 514/716; 514/727; 514/740; 514/742; 514/523
[58] Field of Search ........... 514/716, 727, 740, 742, 514/223.5, 223.2, 523

[56] References Cited

U.S. PATENT DOCUMENTS 4,973,474 11/1990 Hocquaux et al. ............. 424/70
4,985,425 1/1991 Chiba et al. ................. 514/222.2

FOREIGN PATENT DOCUMENTS 61-37717 2/1986 Japan .
62-190116 8/1987 Japan .
62-270519 11/1987 Japan .
64-68309 3/1989 Japan .
2178960 2/1987 United Kingdom .
2211093 6/1989 United Kingdom .

OTHER PUBLICATIONS

Patent Abstracts of Japan, vol. 4, No. 85, Jun. 18, 1980.
Patent Abstracts of Japan, vol. 13, No. 569, Dec. 15, 1989 & JP-A-1 238 515, Sep. 22, 1989.

Primary Examiner—Frederick E. Waddell
Assistant Examiner—Fred Tsung
Attorney, Agent, or Firm—Sprung Horn Kramer & Woods

[57] ABSTRACT

A hair revitalizing tonic composition comprising (i) an amine oxide and (ii) a compound having a calmodulin inhibitory activity and/or a compound having an activity as a calcium antagonist.

1 Claim, No Drawings

HAIR REVITALIZING TONIC COMPOSITION

TECHNICAL FIELD

The present invention relates to a novel hair revitalizing tonic composition, and more specifically, it relates to a hair revitalizing tonic composition comprising an amine oxide, a compound having a calmodulin inhibitory activity and/or a compound having an activity as a calcium antagonist.

BACKGROUND ART

It is generally believed that baldness and a falling-out of hair are caused by (1) an activation of androgens in organs such as the hair roots and sebaceous glands, (2) a lowering of blood flow to the hair follicles, (3) an abnormality of the scalp due to an excessive secretion of sebum, formation of peroxides, or propagation of bacteria or the like, (4) heredodiathesis, (5) neuroses due to stress or the like, (6) side effects of diseases, and (7) aging.

Accordingly, conventional hair revitalizing tonic compositions generally contain a compound by which the above-mentioned causes are eliminated or alleviated. For example, a compound capable of inhibiting the activation of androgens or a compound capable of increasing blood flow to the hair follicles is contained in the hair tonic.

Nevertheless, the mechanisms of loss and regrowth of hair are very complicated, and thus it is impossible to satisfactorily prevent baldness and a falling-out of hair simply by inhibiting the activation of androgens or by increasing the amount of blood flow to the hair follicles.

DISCLOSURE OF INVENTION

Therefore, an object of the present invention is to solve the above-mentioned problems of the conventional hair revitalizing tonic compositions and to provide a hair revitalizing tonic composition which provides an excellent effect of preventing hair loss, and further, of invigorating hair growth.

Other objects and advantages of the present invention will be apparent from the following description.

In accordance with the present invention, there is provided a hair revitalizing tonic compositions comprising (i) an amine oxide and (ii) at least one compound selected from compounds having a calmodulin inhibitory activity and compounds having an activity as a calcium antagonist.

BEST MODE OF CARRYING OUT THE INVENTION

The present inventors carried out research in an attempt to find a compound which would effectively prevent hair loss, and further, having an excellent hair invigorating activity, and as a result, found that a hair revitalizing tonic composition comprising an amine oxide effectively prevents hair loss, and further, invigorates the hair growth. The hair revitalizing tonic composition based on this invention is described in the specification of Japanese Patent Application No. 63-6233. The present inventors then made a further study of the above-mentioned amine oxide, and as a result, found that the effects of preventing hair loss and of invigorating hair growth can be enhanced through the incorporation of the amine oxide in combination with a specific substance. The present invention was completed on the basis of this finding.

Examples of the amine oxide usable in the present invention include the following compounds.

(1) A dimethylalkylamine oxide having the general formula (A):

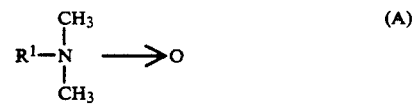

wherein $R^1$ represents a straight-chain or branched alkyl or alkenyl group having 8 to 24 carbon atoms. Specific examples thereof are dimethyllaurylamine oxide, dimethylstearylamine oxide.

(2) A methyldialkylamine oxide having the general formula (B):

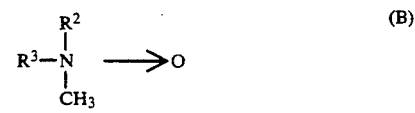

wherein $R^2$ and $R^3$ each independently represent a straight-chain or branched alkyl or alkenyl group having 6 to 18 carbon atoms. Specific examples thereof are didecylamine oxide and didodecylamine oxide.

(3) A dihydroxyethylalkylamine oxide having the general formula (C):

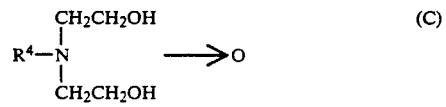

wherein $R^4$ represents a straight-chain or branched alkyl or alkenyl group having 8 to 24 carbon atoms. Specific examples thereof are dihydroxyethyllaurylamine oxide.

(4) A dimethylalkylpolyoxyethyleneamine oxide having the general formula (D):

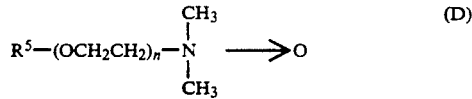

wherein $R^5$ represents a straight chain or branched alkyl or alkenyl group having 8 to 24 carbon atoms and n is an integer of 1 to 5. Specific examples thereof are dimethyllaurylethoxyamine oxide.

(5) An amidopropylalkyldimethylamine oxide having the general formula (E):

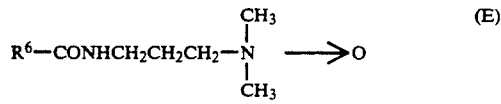

wherein $R^6$ represents a straight-chain or branched alkyl or alkenyl group having 8 to 24 carbon atoms. Specific examples thereof are dimethyllaurylamidopropylamine oxide.

The amine oxides having the above-mentioned general formulae (A) to (E) may be used alone or in any combination thereof.

The "compound having a calmodulin inhibitory activity", i.e., the calmodulin inhibitor, to be used in the present invention includes all compounds which interact with calmodulin, selectively inhibit the enzymes activated by calcium - calmodulin, and promote the tonicity of mammalian hair.

Specific examples of the calmodulin inhibitors are phenothiazine, thioxanthene, butyrophenone, diphenylbutylamine, dibenzodiazepine, benzodiazepine, dibenzazepine, naphthalenesulfonamide, N-(6-aminohexyl)-5-chloro-1-naphthalenesulfonamide, trifluoperazine, chlorpromazine, prenylamine, butaclamol, amitryptyline, ferodipine, vinblastine, vincristine, fluphenazine, pimozide, medazepam, protriptyline, (1-[bis(p-chlorophenyl)methyl]-3-[2,4-dichloro-$\beta$(2,4-dichlorobenzyloxy)phenethyl]imidazolinium chloride, flupentixol, chlorprothixene, haloperidol, chlordiazepoxide, tetracaine, lidocaine, dibucaine, desipramine, clozapine, prumetazine, phentolamine, imipramine, and benperidol.

The calcium antagonist usable in the present invention includes all compounds which control the calcium channel mainly dependent upon the membrane potential in an organism, i.e., the channel actuated by the depolarization of cell membrane and allowing the calcium ions extra to flow into the cells, which inhibit the release of calcium ions from intracellular calcium storage, and which can promote the revitalization of mammalian hair.

Specifically, the following compounds are included.

(1) 1,4-Dihydropyridine derivatives:
Preferred examples thereof are nifedipine, nicardipine, niludipine, nimodipine, nisoldipine, nitrendipine, milbadipine, dazodipine, and ferodipine.

(2) N-Methyl-N-homoveratrilamine derivatives:
Preferred examples thereof are verapamil, gallopamil, and tiapamil.

(3) Benzothiazepine derivatives:
Preferred examples thereof include diltiazem.

(4) Piperazine derivatives:
Preferred examples thereof are cinnarizine, lidoflazine, and flunarizine.

(5) Diphenylpropiramine derivatives:
Preferred examples thereof are prenylamine, terodiline, and phendiline.

(6) Benzothiazole phosphonate derivatives:
Preferred examples thereof are diethyl-4-(benzothiazole-2-yl)benzyl phosphonate.phostedyl.

(7) Bepridil derivatives:
Preferred examples thereof are bepridil.

(8) Perhexyline derivatives:
Preferred examples thereof are perhexyline.

(9) Others:
Examples thereof are 3,4,5-trimethoxybenzoic acid 8-(diethylamino)octyl ester.

The hair revitalizing tonic composition of the present invention may be used in the form of a mixture prepared by adding pharmaceutically acceptable additives and other chemicals, in an amount such that the effect of the present invention is not adversely affected, to the essential components thereof, i.e., the above-mentioned amine oxide and calmodulin inhibitor and/or calcium antagonist.

Examples of such additives are antibacterial agents such as hinokitiol, hexachlorophene, phenol, benzalkonium chloride, cetylpyridinium chloride, undecylenic acid, trichlorocarbanilide and bionol; antiphlogistic or algefacient such as glycyrrhizic acid, ammonium salt and other derivatives thereof, allantoin and menthol; and humectants, surfactants, perfumes, antioxidants, U.V. light absorbers and pigments, for example, chemicals such as salicylic acid, zinc, compounds thereof, lactic acid and alkyl esters thereof, animal and vegetable oils such as olive oil, macadamia nut oil and squalane, hydrocarbon oils such as liquid paraffin, ester oils such as isopropyl myristate, cetyl isooctanoate and 2-ethylhexyl palmitate, waxes such as beeswax, oil components such as a higher fatty acids and higher alcohols, water, lactic acid, ethyl ester and other derivatives thereof, polyhydric alcohols such as polyethylene glycol, glycerol and sorbitol, lower alcohols such as ethanol, mucopolysaccharides, and pyrrolidone carboxylates. These may be used alone or in the form of a mixture thereof.

The hair tonic of the present invention may be administered in any form that is suitable for an external application thereof. Examples of such forms are external preparations such as a lotion, a liniment and a milky lotion, or semisolid external preparations such as a cream, an ointment, a paste, a jelly and a spray.

The hair revitalizing tonic composition of the present invention contains 0.0001 to 20% by weight of an amine oxide as an active ingredient and 0.00001 to 10% by weight, preferably 0.0001 to 5% by weight of a compound having a calmodulin inhibitory activity and/or the compound having an activity as a calcium antagonist. The formulation ratio of the amine oxide to the compound having a calmodulin inhibitory activity and/or the compound having an activity as a calcium antagonist is not particularly limited, but preferably is 10000:1 to 1:10000, more preferably 1000:1 to 1:1000 by weight.

The hair revitalizing tonic composition of the present invention is epidermically administered by direct application or by spraying on the skin.

The dose of the hair revitalizing tonic composition of the present invention depends on the age, individual characteristics, and condition of health, and an indiscriminate statement is inappropriate in this regard. Generally, however, the dose for a human per kg of body weight and per day is from 0.0001 to 1 g, preferably from 0.001 to 0.1 g. The above-mentioned dose of the hair revitalizing tonic composition may be administered once each day or the dose may be divided and administered two to four times each day.

EXAMPLES

The method of formulating the hair revitalizing tonic composition of the present invention into a pharmaceutical preparation, and the hair revitalizing effect thereof, will now be described in more detail by way of the following Examples, which should not be construed as limiting the present invention. The "%" in the Examples represents "% by weight".

Examples of Test of Hair Revitalization Effect (1) Test of Hair Regrowth Using Mice (No. 1)

To investigate the hair revitalizing effect of the present invention, a test of the hair regrowth effect was performed on mice. The back of a C3H/HeNCrj male mouse in a telogen phase was shaven, and each of the six kinds of samples indicated in Table 1 was applied in an amount of 0.1 ml once a day. The judgment of the effect was made on the basis of the ratio of the hair regrowth area, measured by photographs.

TABLE 1

| | Composition of Sample Solution |
|---|---|
| 1 | 70% ethanol solution containing 0.2% of dimethyllaurylamine oxide |
| 2 | 70% ethanol solution containing 0.2% of trifluoroperazine |
| 3 | 70% ethanol solution containing 0.5% of verapamil |
| 4 | 70% ethanol solution containing 0.2% of dimethyllaurylamine oxide and 0.2% of trifluoperazine |
| 5 | 70% ethanol solution containing 0.2% of dimethyllaurylamine oxide and 0.5% of verapamil |
| 6 | 70% ethanol solution |

RESULTS

The ratio of the hair regrowth area and the judgment two weeks after the start of the administration are shown in Table 2.

TABLE 2

| Sample | Ratio of hair regrowth area (%) | Judgment |
|---|---|---|
| 1 | 18.3 ± 3.7 | effective |
| 2 | 13.3 ± 4.2 | effective |
| 3 | 12.5 ± 3.9 | effective |
| 4 | 50.8 ± 6.5 | highly effective |
| 5 | 68.4 ± 7.8 | very highly effective |
| 6 | 0.0 ± 0.0 | not effective |

Note:
The data indicates mean ± S.E. (mean ± standard error).

(2) Test of Hair Regrowth Using Mice (No. 2)

Hairs were removed by a hair clipper from the back of a C3H/HeNCrj male mouse in a telogen phase, and each of the six kinds of samples indicated in Table 3 was applied in an amount of 0.1 ml once a day. The judgment of the effect was made on the basis of the ratio of hair regrowth area (%) measured by photographs taken 4 weeks after the start of the administration. The results are shown in Table 3.

TABLE 3

| Sample | Ratio of hair regrowth area (%)[*1] |
|---|---|
| Sol D[*2] | 11.347 ± 2.745 |
| verapamil[*3] 1.0% SolD solution | 86.698 ± 4.312 |
| diltiazem[*3] 1.0% SolD solution | 34.928 ± 4.312 |
| nicardipine[*3] 1.0% SolD solution | 31.061 ± 8.976 |
| cinnarizine[*3] 1.0% SolD solution | 26.446 ± 6.6995 |
| nifedipine[*3] 1.0% SolD solution | 27.273 ± 3.916 |

Note:
[*1]mean ± S.E. (mean ± standard error)
[*2]solution prepared by dissolving 0.55% of dimethyllaurylamine oxide (manufactured by Nippon Oil & Fats Co., Ltd.), 1.5% of decaglycerol-2-isostearate (manufactured by Nippon Chemical Co., Ltd.) and 0.06% of SDS (sodium lauryl sulfate) (manufactured by New Japan Chemical Co., Ltd.) in 90% ethanol
[*3]calcium antagonist (3) Test of Hair Regrowth Using Mice (No. 3)

Hairs were removed by a hair clipper from the back of C3H/HeNCrj male mouse in a telogen phase, and each of the seven kinds of samples indicated in Table 4 was applied in an amount of 0.1 ml once a day. The judgment of the effect was made on the basis of the ratio of hair regrowth area (%) measured by photographs taken 31 days after the start of the administration. The results are shown in Table 4.

TABLE 4

| Sample | Ratio of hair regrowth area (%)[*1] |
|---|---|
| ethanol | 0.47 ± 0.847 |
| Sol D[*2] | 30.350 ± 11.848 |
| TMB-[*3] | 38.916 ± 14.439 |
| W-7[*4] 0.5% SolD solution | 40.653 ± 5.511 |
| verapamil chloride[*5] 0.5% SolD solution | 80.101 ± 6.588 |

Note:
[*1]mean ± standard error
[*2]see "Note" of Table 3
[*3]calcium antagonist: [3,4,5-trimethoxybenzoic acid 8-(diethylamino)octyl ester]
[*4]calmodulin inhibitor (manufactured by SIGMA)
[*5]calcium antagonist: [N-(6-aminohexyl)-5-chloro-1-naphthalenesulfonamide]

(4) Test of Hair Regrowth Using Mice (No. 4)

Hairs were removed by a hair clipper from the back of C3H/HeNCrj male mouse in a telogen phase, and each of the four kinds of samples indicated in Table 5 was applied in an amount of 0.1 ml once a day. The judgment of the effect was made on the basis of the ratio of hair regrowth area (%) measured by photographs taken 52 days after the start of the application. The results are shown in Table 5.

TABLE 5

| Sample | Ratio of hair regrowth area (%)[*1] |
|---|---|
| Sol D[*2] | 14.243 ± 5.268 |
| verapamil chloride[*3] 3% SolD solution | 85.266 ± 4.236 |
| flunarizine[*4] 3% SolD solution | 49.402 ± 6.009 |

Note:
[*1]mean ± standard error
[*2]see "Note" of Table 3
[*3]calcium antagonist (manufactured by SIGMA)
[*4]calcium antagonist (manufactured by SIGMA)

As apparent from the above-mentioned results, hair revitalizing tonic compositions comprising an amine oxide, a compound having a calmodulin inhibitory activity and/or a compound having an activity as a calcium antagonist exhibit a significant effect, which substantiates that the hair revitalizing tonic compositions according to the present invention have an excellent hair revitalizing effect.

| Example 1: Lotion | |
|---|---|
| 95% ethanol | 80.0 |
| trifluoperazine | 0.01 |
| dimethyllaurylamine oxide | 0.2 |
| sodium lauryl sulfate | 0.06 |
| ethylene oxide (40 mol) adduct of hydrogenated castor oil | 0.5 |
| purified water | 19.23 |
| perfume and pigment | q.s. |

Trifluoperazine, ethylene oxide (40mol) adduct of hydrogenated castor oil and perfume were dissolved in 95% ethanol. Subsequently, purified water was added to the resultant solution, and dimethyllaurylamine oxide, sodium lauryl sulfate and pigment were then added thereto. The mixture was then stirred for dissolution, to thereby prepare a transparent liquid lotion.

| Example 2: Milky Lotion |
|---|
| (Phase A) |

| Example 2: Milky Lotion | |
| --- | --- |
| spermaceti | 0.5 |
| cetyl alcohol | 2.0 |
| vaseline | 5.0 |
| squalane | 10.0 |
| polyoxyethylene (10 mol) monostearate | 2.0 |
| sorbitan monooleate | 1.0 |
| naphthalenesulfonamide | 0.1 |
| dimethylstearylamine oxide | 1.0 |
| (Phase B) | |
| glycerol | 10.0 |
| purified water | 68.2 |
| perfume, pigment and preservative | q.s. |

The phases A and B were each heat-melted and kept at 80° C. Thereafter, both phases were mixed with each other and emulsified, and cooled to room temperature while stirring, to thereby prepare a milky lotion.

| Example 3: Cream | |
| --- | --- |
| (Phase A) | |
| liquid paraffin | 5.0 |
| cetostearyl alcohol | 5.5 |
| vaseline | 5.5 |
| glycerol monostearate | 3.0 |
| polyoxyethylene (20 mol) 2-octyldodecyl ether | 3.0 |
| propylparaben | 0.3 |
| (Phase B) | |
| fluphenazine | 0.001 |
| dimethylcetylamine oxide | 10.0 |
| glycerol | 7.0 |
| dipropylene glycol | 20.0 |
| polyethylene glycol 4000 | 5.0 |
| sodium hexametaphosphate | 0.005 |
| purified water | q.s. |

The phase A was heat-melted and kept at 70° C., and the phase B was added to the phase A and stirred. The resultant emulsion was then cooled to thereby prepare a cream.

| Example 4: Hair Revitalizing Tonic Preparation in Milky Lotion Form | |
| --- | --- |
| (Phase A) | |
| squalane | 9.0 |
| cetyl alcohol | 2.0 |
| vaseline | 5.0 |
| sorbitan monooleate | 1.0 |
| prenylamine | 0.1 |
| dimethylstearylamine oxide | 1.0 |
| polyoxyethylene (10 mol) monostearate | 1.5 |
| (Phase B) | |
| glycerol | 12.0 |
| purified water | 68.4 |

The phases A and B were each heat-melted, mixed with each other, and emulsified by a homomixer, to thereby prepare a hair revitalizing tonic preparation in a milky lotion form.

| Example 5: Lotion | |
| --- | --- |
| 95% ethanol | 80.0 |
| trifluoperazine | 0.01 |
| didecylamine oxide | 0.2 |
| sodium lauryl sulfate | 0.06 |
| ethylene oxide (40 mol) adduct of hydrogenated castor oil | 0.5 |
| purified water | 19.23 |
| perfume and pigment | q.s. |
| Trifluoperazine, ethylene oxide | (40 mol) | adduct of hydrogenated castor oil and perfume were dissolved in 95% ethanol, and thereafter, purified water was added to the resultant solution, and didecylamine oxide, sodium lauryl sulfate and pigment were then added thereto. The mixture was then stirred for dissolution, to thereby prepare a transparent liquid lotion.

| Example 6: Milky Lotion | |
| --- | --- |
| (Phase A) | |
| spermaceti | 0.5 |
| cetyl alcohol | 2.0 |
| vaseline | 5.0 |
| squalane | 10.0 |
| polyoxyethylene (10 mol) monostearate | 2.0 |
| sorbitan monooleate | 1.0 |
| didodecylamine oxide | 0.1 |
| naphthalenesulfonamide | 0.5 |
| dimethylstearylamine oxide | 1.0 |
| nifedipine | 0.1 |
| lidocaine | 0.001 |
| (Phase B) | |
| glycerol | 10.0 |
| purified water | 68.2 |
| perfume, pigment and preservative | q.s. |

The phases A and B were each heat-melted and kept at 80° C. Thereafter, both phases were mixed with each other and emulsified, and then cooled to room temperature while stirring, to thereby prepare a milky lotion.

| Example 7: Cream | |
| --- | --- |
| (Phase A) | |
| liquid paraffin | 5.0 |
| cetostearyl alcohol | 5.5 |
| vaseline | 5.5 |
| glycerol monostearate | 3.0 |
| polyoxyethylene (20 mol) 2-octyldodecyl ether | 3.0 |
| propylparaben | 0.3 |
| (Phase B) | |
| fluphenazine | 5.0 |
| dimethylcetylamine oxide | 0.005 |
| glycerol | 7.0 |
| dipropylene glycol | 20.0 |
| polyethylene glycol 4000 | 5.0 |
| sodium hexametaphosphate | 0.005 |
| purified water | q.s. |

The phase A was heat-melted and kept at 70° C., and the phase B was added to the phase A and stirred. The resultant emulsion was then cooled to thereby prepare a cream.

| Example 8: Hair Revitalizing Tonic Preparation in Milky Lotion Form | |
| --- | --- |
| (Phase A) | |
| squalane | 9.0 |
| cetyl alcohol | 2.0 |
| vaseline | 5.0 |
| sorbitan monooleate | 1.0 |
| diltiazem | 0.6 |
| cinnarizine | 0.3 |
| dihydroxyethyllaurylamine oxide | 0.0004 |

-continued

| Example 8: Hair Revitalizing Tonic Preparation in Milky Lotion Form | |
|---|---|
| polyoxyethylene (10 mol) monostearate | 1.5 |
| (Phase B) | |
| glycerol | 12.0 |
| purified water | 68.4 |

The phases A and B were each heat-melted, mixed with each other, and emulsified by a homomixer, to thereby prepare a hair tonic preparation in a milky lotion form.

| Example 9: Lotion | |
|---|---|
| 95% ethanol | 80.0 |
| phenothiazine | 0.0005 |
| diazepam | 0.0005 |
| dimethyllaurylethoxyamine oxide | 1.0 |
| sodium lauryl sulfate | 0.06 |
| ethylene oxide (40 mol) adduct of hydrogenated castor oil | 0.5 |
| purified water | 19.23 |
| perfume and pigment | q.s. |

Phenothiazine, diazepam, ethylene oxide (40 mol) adduct of hydrogenated castor oil and perfume were dissolved in 95% ethanol, and thereafter, purified water was added to the resultant solution, and dimethyllaurylethoxyamine oxide, sodium lauryl sulfate and pigment were then added thereto. The mixture was then stirred for dissolution, to thereby prepare a transparent liquid lotion.

| Example 10: Milky Lotion | |
|---|---|
| (Phase A) | |
| spermaceti | 0.5 |
| cetyl alcohol | 2.0 |
| vaseline | 5.0 |
| squalane | 10.0 |
| polyoxyethylene (10 mol) monostearate | 2.0 |
| sorbitan monooleate | 1.0 |
| dimethyloctylamine oxide | 0.1 |
| naphthalenesulfonamide | 0.1 |
| dimethylstearylamine oxide | 0.1 |
| nifedipine | 0.1 |
| (Phase B) | |
| glycerol | 10.0 |
| purified water | 68.2 |
| perfume, pigment and preservative | q.s. |

The phases A and B were each heat-melted and kept at 80° C. Thereafter, both phases were mixed with each other and emulsified, and then cooled to room temperature while stirring, to thereby prepare a milky lotion.

| Example 11: Hair Revitalizing Tonic Preparation in Milky Lotion Form | |
|---|---|
| (Phase A) | |
| squalane | 9.0 |
| cetyl alcohol | 2.0 |
| vaseline | 5.0 |
| sorbitan monooleate | 1.0 |
| TMB-8 [3,4,5-trimethoxybenzoic acid 8-(diethylamino)octyl ester | 0.1 |
| dimethylstearylamine oxide | 1.0 |
| polyoxyethylene (10 mol) monostearate | 1.5 |
| (Phase B) | |

-continued

| Example 11: Hair Revitalizing Tonic Preparation in Milky Lotion Form | |
|---|---|
| glycerol | 12.0 |
| purified water | 68.4 |

The phases A and B were each heat-melted, mixed with each other, and emulsified by a homomixer, to thereby prepare a hair revitalizing tonic preparation in a milky lotion form.

INDUSTRIAL APPLICABILITY

The hair revitalizing tonic composition of the present invention comprising a combination of an amine oxide with a compound having a calmodulin inhibitory activity and/or a compound having an activity as a calcium antagonist provides a far superior hair revitalizing effect due to the use of a combination of said components, compared to the case where said components are used alone.

We claim:

1. A hair revitalizing tonic composition comprising Verapamil and at least one amine oxide selected from the group consisting of amine oxides having the formulae (A), (B), (C) and (D):

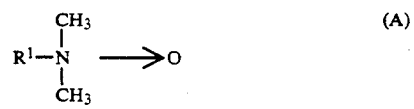

(A)

wherein $R^1$ represents a straight-chain or branched alkyl or alkenyl group having 8 to 24 carbon atoms;

(B)

wherein $R^2$ and $R^3$ each independently represent a straight-chain or branched alkyl or alkenyl group having 6 to 18 carbon atoms;

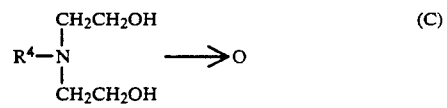

(C)

wherein $R^4$ represents a straight-chain or branched alkyl or alkenyl group having 8 to 24 carbon atoms;

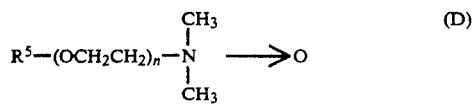

(D)

wherein $R^5$ represents a straight chain or branched alkyl or alkenyl group having 8 to 24 carbon atoms and n is an integer of 1 to 5; and

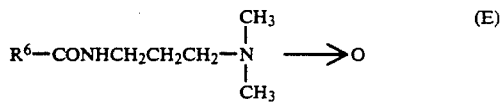

(E)

wherein $R^6$ represents a straight-chain or branched alkyl or alkenyl group having 8 to 24 carbon atoms wherein the weight ratio of the amine oxide to the Verapamil is from 10,000:1 to 1:10,000.

* * * * *